US005360782A

United States Patent [19]
Young et al.

[11] Patent Number: 5,360,782
[45] Date of Patent: * Nov. 1, 1994

[54] AQUEOUS SOLUTION COMPRISING A THIOCARBONATE, A SULFIDE, AND AN AMMONIACAL COMPOUND

[75] Inventors: Donald C. Young, Fullerton, Calif.; James A. Green, II, Maipu, Chile

[73] Assignee: Union Oil Company of California, Los Angeles, Calif.

[*] Notice: The portion of the term of this patent subsequent to Nov. 24, 2008 has been disclaimed.

[21] Appl. No.: 141,390

[22] Filed: Oct. 22, 1993

Related U.S. Application Data

[63] Continuation of Ser. No. 982,155, Nov. 25, 1992, which is a continuation of Ser. No. 663,362, Feb. 28, 1991, abandoned, which is a continuation-in-part of Ser. No. 262,961, Oct. 28, 1988, Pat. No. 5,041,240, and a continuation-in-part of Ser. No. 262,962, Oct. 28, 1988, abandoned, and a continuation-in-part of Ser. No. 128,146, Dec. 3, 1987, Pat. No. 5,022,912, which is a continuation-in-part of Ser. No. 685,454, Nov. 16, 1984, Pat. No. 4,726,144, which is a continuation-in-part of Ser. No. 315,492, Oct. 27, 1981, Pat. No. 4,476,113.

[51] Int. Cl.$^5$ .............. C05G 3/02; A01N 59/02; A01N 59/04; A01N 59/26
[52] U.S. Cl. ............. 504/101; 424/40; 424/42; 424/606; 424/699; 424/701; 424/703; 424/706; 424/707; 424/710; 424/713; 424/715; 424/718; 424/719; 424/721; 424/722; 47/58; 47/DIG. 10; 514/512
[58] Field of Search ............ 424/606, 699, 701, 703, 424/706, 707, 713, 715, 719, 722, 40, 42, 710, 718, 721; 47/58, DIG. 10; 504/101; 514/512

[56] References Cited

U.S. PATENT DOCUMENTS

| | | | |
|---|---|---|---|
| 1,044,452 | 11/1912 | Halland | 424/705 |
| 2,046,128 | 6/1936 | McQuiston | 167/20 |
| 2,676,129 | 4/1954 | Bashour | 167/22 |
| 2,731,487 | 1/1956 | Bashour | 260/455 |
| 2,836,532 | 5/1958 | Seifter | 167/14 |
| 2,836,533 | 5/1958 | Seifter | 167/14 |
| 3,133,857 | 5/1964 | Swezey | 167/39 |
| 3,837,304 | 9/1974 | Carroll | 111/6 |
| 3,852,220 | 12/1974 | Kimmel et al. | 252/524 |
| 3,892,741 | 7/1975 | Taylor | 260/246 B |
| 4,006,056 | 2/1977 | Weber | 424/72 |
| 4,042,501 | 8/1977 | King | 210/51 |
| 4,078,912 | 3/1978 | Hawkins | 71/28 |
| 4,435,304 | 3/1984 | Lindstsrom et al. | 252/156 |
| 4,476,113 | 10/1984 | Young et al. | 424/161 |
| 4,551,167 | 11/1985 | Young et al. | 71/64.1 |
| 4,726,144 | 2/1988 | Young et al. | 47/58 |
| 4,908,142 | 3/1990 | Dumdum et al. | 252/17 |
| 4,908,143 | 3/1990 | Dumdum et al. | 252/17 |

(List continued on next page.)

FOREIGN PATENT DOCUMENTS 1501516 2/1978 United Kingdom.

OTHER PUBLICATIONS

Farm Chemicals Handbook '75, Dictionary of Plant Foods, Meister Publishing Co., 1975, Ohio, pp. B12, B15–B18, B23 and B67.

(List continued on next page.)

*Primary Examiner*—Gary E. Hollinden
*Assistant Examiner*—John D. Pak
*Attorney, Agent, or Firm*—Gregory F. Wirzbicki; Shlomo R. Frieman

[57] ABSTRACT

Aqueous thiocarbonate solutions are stabilized by the addition of base, sulfide and/or polysulfide, and the stability and safety of the more concentrated solutions containing 1 weight percent or more equivalent $CS_2$ as a thiocarbonate are achieved as reflected by significant reduction of $CS_2$ partial pressure in such solutions. Also, deposit formation in irrigation systems delivering such thiocarbonates, such as drip emitters and sprinkler heads, is reduced or eliminated with minor amounts of sodium hexametaphosphate.

16 Claims, No Drawings

U.S. PATENT DOCUMENTS

| | | |
|---|---|---|
| 5,013,350 | 5/1991 | Green et al. ............................. 71/65 |
| 5,022,912 | 6/1991 | Young et al. ........................... 71/30 |
| 5,039,327 | 8/1991 | Pilling et al. ........................... 71/27 |
| 5,041,240 | 8/1991 | Green, II et al. ................... 424/703 |
| 5,076,358 | 12/1991 | Kissel ................................. 166/275 |
| 5,112,623 | 5/1992 | Green et al. ........................ 424/713 |
| 5,165,920 | 11/1992 | Green, II et al. ................ 424/78.37 |
| 5,167,966 | 12/1992 | Green, II et al. .................. 424/715 |
| 5,173,306 | 12/1992 | Green, II et al. .................. 424/703 |
| 5,190,677 | 3/1993 | Pilling et al. .......................... 252/17 |
| 5,256,424 | 10/1993 | Green, II et al. .................. 424/701 |

OTHER PUBLICATIONS

Zins et al., *C. R. Acad. Sc. Paris*, t276 (Mar. 12, 1973), pp. 951–954.

Yeoman, *Journal of the Chemical Society*, vol. 199, pp. 38–54, (1921).

Ashworth et al., *Inhibition of Nitrification by Nitrapyrin, Carbon Disulfide and Trithiocarbonate*, J. Sci. Fd. Agric. 1977, 28, 673–683.

*Agricultural Chemicals—Book III, Miscellaneous Chemicals*, 1976–77, W. R. Thomson, Thomson Publications, P.O. Box 7964, Fresno, Calif. (1970), pp. 11–12.

*Agricultural Chemicals—Book IV, Fungicides*, 1976–77 Revision, W. R. Thomson, Thomas Publications, P.O. Box 7964, Fresno, Calif. (1976), pp. 15–16.

O'Donoghue and Kahan, "Thiocarbonic Acid and Some of Its Salts," Journal of the Chemical Society, vol. 89 (II), pp. 1812–1818 (1906).

Mills and Robinson, "Ammonium Polysulphides, Hydrogen Pentasulphide, and the Thiocarbonic Acids," *Journal of the Chemical Society*, vol. 1928 (II) pp. 2326–2332 (1928).

"The Soil Pest Complext," *Agricultural and Food Chemistry*, vol. 3, pp. 202–205, (1955).

Soil Biology and Biochemistry, J. M. Bremner and L. G. Bundy, vol. 6, pp. 161–165, (1974).

*Chemistry and Industry*, J. Ashworth et al., Sep. 6, 1975, pp. 749–750.

*Chemical Abstracts*, vol. 87, 1977, No. 87:16857s, "Effect of Pyridine, Toluene and Carbon Disulfide on the Growth of Nitrifying Bacteria in Omeliansky's Medium" Cited in U.S. Pat. No. 4,551,167.

*Chemical Abstracts*, vol. 99, 1983, No. 99:138732r, cited in U.S. Pat. No. 4,551,167.

Miall's Dictionary of Chemistry, 5th Ed. Great Britain, Longman Group Ltd., (1981), p. 459.

The Merck Index, 8th Ed., Rahway, N.J., Merck & Co. Inc., (1968), p. 960.

The Condensed Chemical Dictionary, 6th Ed. Reinhold Publishing Corp., N.Y., N.Y. (1965, p. 1223.

AQUEOUS SOLUTION COMPRISING A THIOCARBONATE, A SULFIDE, AND AN AMMONIACAL COMPOUND

CROSS-REFERENCES TO RELATED APPLICATIONS

This application is a continuation of application Ser. No. 07/982,155, filed Nov. 25, 1992, which is a continuation of application Ser. No. 07/663,362, filed Feb. 28, 1991, now abandoned, which is a continuation-in-part of our copending applications (a) Ser. No. 07/262,961, filed Oct. 28, 1988, now U.S. Pat. No. 5,041,240, (b) Ser. No. 07/262,962, filed Oct. 28, 1988, now abandoned, and (c) Ser. No. 07/128,146, filed Dec. 3, 1987, now U.S. Pat. No. 5,022,912, Ser. No. 07/128,146 being a continuation-in-part of Ser. No. 06/685,454, filed Nov. 16, 1984 (and based on application PCT/US/00650 filed Apr. 30, 1984), now U.S. Pat. No. 4,726,144, which is a continuation-in-part of Ser. No. 315,492, filed Oct. 27, 1981, now U.S. Pat. No. 4,476,113, the foregoing documents being incorporated herein in their entireties by reference.

TECHNICAL FIELD

This invention relates to the field of stabilized thiocarbonate compositions and, in particular, to stabilized, aqueous thiocarbonate solutions and to methods of using such compositions. It also relates to thiocarbonate compositions stabilized against hardwater component precipitation and irrigation system plugging.

INTRODUCTION

Among the more economically serious plant parasites are nematodes, which are roundworms, comprising as many as 10,000 species, of which at least 150 are known to adversely affect plant life. Plant parasitic nematodes have been known since about the year 1750. Most of the nematodes which cause crop damage do so by feeding on plant roots, and therefore are found primarily in the upper few inches of soil in the roots or in close proximity to the roots. Nematode feeding causes hypertrophy or gall formation, and the evidence of heavy infestation is plant stunting, pale foliage, wilting, and even plant death in extreme cases.

Virtually all of the world's crops and ornamental plants can be attacked by parasitic nematodes. Important destructive nematode species include the root knot nematodes which are hosted by tomatoes, alfalfa, cotton, corn, potatoes, citrus and many other crops, the golden nematode of potatoes, the sugar beet cyst nematode and the citrus nematode. These, and a few other species, are described in "The Soil Pest Complex", *Agricultural and Food Chemistry*, Vol. 3, pages 202–205 (1955). Also described therein is a further complication resulting from nematode infestation, namely a lowered resistance to the effects of plant attack by bacteria and pathogenic soil fungi.

Except for small volumes of soil which can be sterilized, it has not been found possible to eliminate nematodes. Parasite populations can, however, be kept at levels which economically permit agricultural operations by soil fumigation, crop rotation using non-hosting plant varieties, and (to a much lesser extent) the development of plants which are resistant to infestation. In many instances, control of nematodes is achieved only by combinations of these techniques, and most control programs have proven quite costly.

Another serious problem in agriculture is the attack of plants by pathogenic microorganisms, particularly fungi. Such pathogens are normally controlled by fumigation, prior to crop planting, using broad spectrum biocides, many of which are no longer regarded as environmentally safe. Certain narrow spectrum fungicides are available, but are extremely expensive and lose effectiveness against successive generations of fungi, due to genetic adaptability.

Carbon disulfide is the first reported soil fumigant, used in Europe during the 1870's to control the sugar beet nematode. This agent is commercially impractical, however, since very large quantities must be applied, due to its high volatility. Further, the material is quite flammable, reportedly being ignited even by static electricity resulting from pouring the material out of drums. In addition, carbon disulfide possesses a very objectionable odor, and its vapors are toxic to humans. When sold for fumigant use, the carbon disulfide is normally mixed with an inert fire retarding compound, such as carbon tetrachloride, and occasionally also with another fumigant. Typically, these compositions do not contain over about 20 percent by weight of carbon disulfide.

In addition to soil uses, carbon disulfide has been proven effective in the fumigation of commodities, as an insecticide, as a rodenticide, and for controlling certain weeds.

Numerous compositions possessing nematocidal properties have been developed, including active ingredients such as the polyamines of U.S. Pat. No. 2,979,434 to Santmyer, the heterocyclic compounds of U.S. Pat. No. 2,086,907 to Hessel, and various halogenated compounds. Among the useful halogen-containing nematocides are 1,2-dibromoethane, methyl bromide, 3-bromopropyne, 1,2-dichloropropane, ethylene dichloride and others, all of which are quite phytotoxic, therefore restricting their utility to mostly preplant treatments.

One compound which enjoyed considerable commercial success is 1,2-dibromo-3-chloropropane (DBCP), which can be used to control nematodes in soils with growing perennial plants. However, use of this material has been limited due to a finding of undesirable reproductive system effects in workers exposed to the chemical, and the possibility that the compound is a carcinogen. The unavailability of DBCP has been a serious setback to growers of perennial crops, such as grapes, stone fruits and nuts, since these crops experience more severe cumulative nematode population increases, and most replacement soil fumigants are phytotoxic. U.S. patents concerned with the use of DBCP as a soil fumigant include U.S. Pat. No. 2,937,936 to Schmidt and U.S. Pat. No. 3,049,472 to Swezey.

A further class of materials used to control nematodes includes some thiocarbonates. U.S. Pat. No. 2,676,129 to Bashour describes the preparation of lower aliphatic disubstituted trithiocarbonates having the structure as in (1):

wherein $R_1$ and $R_2$ are alkyl radicals having from three to nine carbon atoms. The compounds were dissolved in acetone and added to nematode-infested coils, resulting in control of the nematodes.

Other compounds have been reported by Seifter in U.S. Pat. Nos. 2,836,532 and 2,836,533, the former relating to the use of sodium and potassium trithiocarbonate, and the latter pertaining to alkali metal and ammonium salts of tetrathioperoxycarbonic acid. Both are described as effective in nematode control. These references state that "not all carbon disulfide derivatives are effective nematode toxicants." Furthermore, U.S. Pat. No. 2,836,532 points out that sodium trithiocarbonate is unexpectedly superior to potassium trithiocarbonate as a nematocide.

The chemistry of thiocarbonic acids and salts has been studied in some detail, as indicated in the papers by O'Donoghue and Kahan, *Journal of the Chemical Society*, Vol. 89 (II), pages 1812–1818 (1906); Yeoman, *Journal of the Chemical Society*, vol. 119, pages 38–54 (1921); and Mills and Robinson, *Journal of the Chemical Society*, Vol. 1928 (II), pages 2326–2332 (1928). According to O'Donoghue and Kahan, derivatives of thiocarbonic acid were prepared by Berzelius, who reacted aqueous solutions of hydrosulfides with carbon disulfide, the reactions occurring as in (2):

$$2\ KHS + CS_2 \rightarrow K_2CS_3 + H_2S \qquad (2)$$

giving unstable solutions which yielded unstable crystalline salts.

Other thiocarbonates were prepared and further characterized by O'Donoghue and Kahan. Their paper, at page 1818, reports the formation of ammonium thiocarbonate by reacting liquid ammonia with cold alcoholic thiocarbonic acid, prepared by dropping a solution of "calcium thiocarbonate" into concentrated hydrochloric acid. The "calcium thiocarbonate" utilized by the authors is described as a double salt, including the calcium cation in combination with both hydroxide and trithiocarbonate anions.

The noted paper by Yeoman reports the further study of thiocarbonates (called trithiocarbonates therein) and also reports the preparation and properties of perthiocarbonates (or tetrathiocarbonates), derivatives of tetrathiocarbonic acid, $H_2CS_4$. Yeoman prepared ammonium trithiocarbonate by saturating an alcoholic ammonia solution with hydrogen sulfide, and then adding carbon disulfide; dry ether was added to precipitate the product salt. Ammonium perthiocarbonate was prepared in a similar manner, except that after reacting the ammonia and hydrogen sulfide, elemental sulfur was added to form the disulfide, $(NH_4)_2S_2$; adding carbon disulfide immediately precipitated the product.

Yeoman states that "solutions of both ammonium trithiocarbonate and perthiocarbonate are very unstable" due to both decomposition to form thiocyanate as a product, and to "complete dissociation into ammonia, hydrogen sulfide, and carbon disulfide."

Considerable explanation is provided concerning the stability of thiocarbonates, as exemplified by sodium trithiocarbonate and perthiocarbonate. Sodium trithiocarbonate solutions in water are said to remain stable only if oxygen and carbon dioxide are "rigidly excluded"; the presence of oxygen causes decomposition to form carbon disulfide and thiosulfates, while carbon dioxide decomposes the solution to give a carbonate and carbon disulfide. Similarly, solutions of sodium perthiocarbonate are reported to be stable for a considerable time in the absence of oxygen, the presence of air causing decomposition into thiosulfate and carbon disulfide, while carbon dioxide decomposes the compound to form a carbonate, elemental sulfur, carbon disulfide, and hydrogen sulfide. The potassium thiocarbonates behave similarly, according to Yeoman.

Yeoman also attempted to prepare and characterize the stability of thiocarbonate salts of four of the alkaline earth metals. Yeoman was unable to prepare a "pure" calcium tri- or tetrathiocarbonate, but observed that the double salt of calcium trithiocarbonate that he prepared was more stable (probably because it was less hygroscopic) than the sodium or potassium thiocarbonates. The barium tetrathiocarbonate could not be isolated, although Yeoman believed that it existed in solution. Barium trithiocarbonate was found to be stable, although it was alleged to behave like sodium trithiocarbonate when dissolved in water. The preparation of aqueous solutions of the tri- and tetrathiocarbonate of magnesium and strontium was alleged, but the magnesium thiocarbonates were not characterized. However, the stability of none of the magnesium or strontium salts or solutions was determined.

The previously noted paper by Mills and Robinson discusses the preparation of ammonium thiocarbonate by digesting ammonium pentasulfide (obtained by suspending sulfur in aqueous ammonia, then saturating with hydrogen sulfide) with carbon disulfide. A crystalline residue from this digestion was found to be ammonium perthiocarbonate. These authors prepared a "better" ammonium perthiocarbonate product, however, by extracting the ammonium pentasulfide with carbon disulfide in a Soxhlet apparatus.

Another serious problem in agriculture is that of low nitrogen use-efficiency, since crops have been found to recover only 30 to 70 percent of the total amount of expensive fertilizer nitrogen which is applied to the soil. Most of the lost nitrogen is due to nitrite and nitrate ions, which are exceptionally mobile in a soil environment, and therefore are readily lost by surface runoff and also by leaching from the plant root zone into deeper soil. Other losses of these ions are due to denitrification, which is reduction to elemental nitrogen or gaseous nitrogen oxides under conditions of limited aeration. In addition to the direct economic losses, these nitrogen forms constitute environmental pollutants when runoff enters surface and ground water systems.

Although some nitrogen is applied to soil in the form of nitrate (e.g., ammonium nitrate-containing fertilizers), most nitrogen fertilization is with ammonia, ammonium compounds other than nitrate and urea materials. Ammonium nitrogen is fairly tightly bound by various physical and chemical processes in a soil environment and, therefore, is much less subject to losses. Unfortunately, the bound ammonium nitrogen is also less available to plants.

The process of nitrification results in conversion of ammonium ions into nitrate ions. Microbial species known as nitrosomonas oxidize ammonium to nitrate; nitrobacter species oxidize nitrite to nitrate. This more mobile ion is easily taken up by plant roots and is also readily assimilated by plant. In this regard, the nitrification process is desirable, but control of the rate at which conversion occurs has not been easily obtained. Inhibition of nitrification would tend to make the applied nitrogen available to plants over a longer period of time, resulting in an increased plant uptake efficiency.

Various compositions have been offered as inhibitors of nitrification, including expensive organic materials such as 2-chloro-6-(trichloromethyl)-pyridine, 2-amino-4-chloro-6-methyl-pyrimidine, sulfathiazoles, alkanolysulfathiazoles, and others. A paper by J. M. Bremner and L. G. Bundy in *Soil Biology and Biochemistry*, vol. 6, pages 161–165 (1974) describes the efficacy of various volatile organic sulfur compounds, including methyl mercaptan, dimethyl sulfide, dimethyl disulfide, carbon disulfide, and hydrogen sulfide. Carbon disulfide in very small amounts is described as having "a remarkable inhibitory effect on nitrification of ammonium in soils incubated in closed systems." Carbon disulfide was tested in the field by J. Ashworth et al., *Chemistry and Industry*, Sep. 6, 1975, pages 749–750, and found to be effective as a nitrification inhibitor. Hawkins, in U.S. Pat. No. 4,078,912, describes the use of sodium, potassium and ammonium trithiocarbonates, and of xanthates, either alone or in fertilizer mixtures, to inhibit nitrification; the mode of operation is attributed to a release of carbon disulfide by the compounds.

One additional potential problem, which could be presented to the agricultural industry in the very near future, is the loss of the widely used, effective fumigant, 1,2-dibromoethane, i.e. ethylene dibromide (EDB), due to environmental concerns. This agent is approved for use on the same crops as is carbon disulfide, and is additionally used extensively in chambers for fumigating fruits and vegetables to control various insects.

In view of the above, it is clear that the chemical behavior of the alkaline earth metal thiocarbonate salts is unpredictable. Moreover, it is clear that there is no method taught in the art for preparing either the trithio- or tetrathio-salt of calcium.

We have found that, while aqueous solutions of thiocarbonates provide a method for delivering and using equivalent carbon disulfide in a much safer form than is the use of carbon disulfide, per se, both the dilute and concentrated, aqueous thiocarbonate solutions have significant carbon disulfide vapor pressures with the consequence that significant $CS_2$ concentrations can occur in the equilibrium vapor space overlying such solutions. For instance, we have found that a stoichiometric, aqueous solution of sodium trithiocarbonate in a concentration corresponding to 12.9 weight percent equivalent carbon disulfide has a $CS_2$ vapor pressure corresponding to an equilibrium $CS_2$ concentration in the vapor phase of 27 volume percent at 24° C. The somewhat more stable stoichiometric, aqueous solution of sodium tetrathiocarbonate, also containing about 12.9 weight percent equivalent $CS_2$, has a vapor pressure corresponding to approximately 14 volume percent $CS_2$ in the vapor phase overlying the solution at 24° C. Such compositions can be very hazardous, particularly in view of the fact that the explosive range of carbon disulfide in air is from 1 to 50 volume percent; i.e. an air-$CS_2$ mixture having a $CS_2$ concentration between 1 and 50 volume percent is explosive. In addition, $CS_2$ is very toxic, and the presence of such high volumes of $CS_2$ in the vapor phase results in significant loss of active, equivalent $CS_2$ in the aqueous solution. We have also found that significant $CS_2$ vapor pressures can occur over more dilute, stoichiometric thiocarbonate solutions.

A need exists for a fluid which can release carbon disulfide for fumigation and nitrification inhibiting purposes, but which can be stored and handled safely and without significant loss of effectiveness during a reasonable commercial storage and delivery cycle.

It is therefore an object of the present invention to provide a stabilized liquid composition which can be caused to release fumigants, including carbon disulfide.

It is a further object to provide a stabilized composition which is miscible with water to form a fumigant and nitrification inhibitor which can be applied to soils by means of fluid handling equipment or introduced into irrigation water.

Another object is provision of concentrated and dilute, aqueous thiocarbonate solutions having reduced $CS_2$ vapor pressures useful for industrial and agricultural applications.

Other objects and advantages will be apparent from the following disclosure.

SUMMARY

The invention is directed to the fumigation of soils, enclosed spaces, agricultural products and other commodities, etc., using compositions which decompose to form carbon disulfide and certain other biocidal materials. Such fumigation can be used to control bacteria, fungi, insects, nematodes, rodents, and weeds, all of which are included herein in the term "pests," and it can be used to inhibit nitrification. We have also found that the use of such thiocarbonates in irrigation water applied through restricted orifices, such as drip emitters and spray nozzles, with "hard" irrigation waters can result in irrigation system plugging and that this problem can be avoided by the addition of sodium hexametaphosphate.

Fumigant compositions are described herein as "thiocarbonates," including, without limitation, salts of trithiocarbonic acid and tetrathiocarbonic acid, compositions having empirical formulae intermediate to these acid salts (such as $MCS_{3.7}$, wherein M is a divalent cation), and compositions containing substances in addition to thiocarbonates [such as a stabilized ammonium tetrathiocarbonate which contains ammonium sulfide, i.e., $(NH_4)_2CS_4 \cdot (NH_4)_2S$]. Stabilized, aqueous thiocarbonate solutions useful for industrial and agricultural applications are also provided which contain an amount of added base sufficient to reduce the vapor pressure of carbon disulfide in the solution. Alternatively, the compositions can contain an amount of added sulfide and/or polysulfide sufficient to reduce the carbon disulfide vapor pressure of the solution, and compositions are also provided which contain combinations of added base and added sulfide and/or polysulfide. Thus, the stabilized aqueous thiocarbonate solutions of this invention involve aqueous solutions of thiocarbonates, soluble in the solution, and having the general formula $A_aCS_b$ wherein A is a mono- or divalent cation, b is 3 to 4, a is 2 when A is a monovalent cation, and a is 1 when A is a divalent cation, and a base and/or a sulfide and/or polysulfide of the formula $M_nS_x$ wherein M is selected from mono- and divalent cations, and combinations thereof, x is at least 1, n is 2 when M is a monovalent cation, and n is 1 when M is a divalent cation. The aqueous solutions can comprise mixtures of tri- and tetrathio-carbonates having the same or different cations as well as mixtures of sulfides and polysulfides of the same or different cations.

The compositions are generally water soluble and can be prepared, stored, and used in aqueous solutions. Thiocarbonate solutions of the invention are stable during prolonged periods of storage in a closed container, exhibit a low vapor pressure, and are not flammable. For soil fumigation, thiocarbonates can be mixed with fertilizers to provide a multi-functional application. Such compositions and methods for their preparation and use are also discussed in our co-pending patent applications Ser. Nos. 07/262,961, filed Oct. 28, 1988, and 07/262,962, filed on the same date, and related compositions and methods of manufacture and use are discussed in our U.S. patent application Ser. No. 07/128,148, filed Dec. 3, 1987 and Ser. No. 06/685,454, filed Apr. 30, 1984 (now U.S. Pat. No. 4,726,144), of which our patent applications Ser. Nos. 07/262,961 and 07/262,962 were continuations-in-part. All of the aforegoing U.S. patent applications are incorporated herein by reference in their entireties.

DETAILED DESCRIPTION

The process of soil fumigation requires the movement of gaseous chemicals through the soil which is treated, and the readily apparent necessity for a sufficient concentration of gas at a given temperature and pressure condition to be lethal to the pest which would be controlled. Volatility of the chemical agent is critical to successful fumigation, since a very volatile substance will disperse too readily and not develop an effective concentration except for locations very close to the point of introduction to the soil. Substances having a very low volatility are also undesirable, since they will not disperse in the soil, and will be effective only at locations near the point of introduction.

Since fumigants typically are effective against a pest only during specific phases in the life cycle of the pest, some measures must be taken to ensure that the fumigant is present during the proper phases. This requirement normally has been met by either applying highly persistent chemicals, applying large enough doses of the chemicals so that the normal decomposition, leaching, volatilization, and other processes will have a lesser effect upon pesticide concentration in the treated environment, or, for highly volatile chemicals, enclosing the treated area (such as by covering soils) for sufficient time to achieve control of the pest. Unfortunately, most of the persistent chemicals are now environmentally undesirable and the noted application methods are sometimes prohibitively expensive.

Stabilized, aqueous thiocarbonate solutions are also provided which contain an amount of added base and/or sulfide or polysulfide sufficient to reduce the carbon disulfide vapor pressure of the solution. Such reduction of $CS_2$ vapor pressure results in and is reflected by a reduction in the $CS_2$ concentration in the equilibrium vapor phase overlying the solutions. Such compositions are particularly useful in agricultural and industrial applications and in the manufacture, storage and transportation of thiocarbonate solutions in that they reduce the hazards associated with $CS_2$ evolution and inhibit thiocarbonate decomposition and consequent $CS_2$ release.

The term "stability", as used herein, can be regarded as a composite of two concepts: chemical stability and physical stability. Since the effectiveness of a composition depends, at least in part, upon its ability to release carbon disulfide during decomposition, chemical stability is expressed accordingly; this can be quantified by, for example, chemically decomposing the composition and measuring the amount of carbon disulfide which evolves. Alternatively, an indication of the amount of available carbon disulfide can be obtained by spectrophotometrically determining the presence of the thiocarbonyl bond

in a sample of the composition. The absorbance at wavelengths corresponding to those at which thiocarbonyl is known to absorb energy can be used for a quantitative analysis.

Symptomatic of chemical stability, but having an independent significance, is physical stability. This concept is important due to the nature of the products formed during decomposition of the composition, particularly the ammonia, hydrogen sulfide, and carbon disulfide, which each have a high vapor pressure. It is readily apparent that a change in the physical form of the composition from a solution of low vapor pressure into a mixture of compounds, each possessing a high vapor pressure, imposes some rather stringent requirements upon storage containers. Vapor pressure above the composition of the invention, therefore, will be used herein as an indicator of physical stability; a condition of maintained low vapor pressure is the desired property. Another index of physical instability is the formation of undesirable insoluble precipitates, which frequently comprise sulfur, or of an immiscible liquid phase, such as carbon disulfide. The more general description of physical stability, then, is the maintenance of only a single phase in the composition.

Assessment of the stability of a particular composition must involve consideration of both the chemical stability and the physical stability over a period of time during which stability is desired. Certain formulations do not form precipitates and do not develop high vapor pressures during a reasonable storage period and, therefore, may be preferred over a formulation which has a greater chemical stability, but develops objectionable physical characteristics during storage. As a further example, a composition which is intended to be used as an additive to irrigation water is likely to be selected for its freedom from precipitate formation upon dilution; to obtain this property, a composition having a lower chemical stability could be necessary.

The useful thiocarbonates include, without limitation, salts of trithiocarbonic acid and tetrathiocarbonic acid, compositions having empirical formulae intermediate to these acid salts (such as $MCS_{3.7}$, wherein M is a divalent metal ion), and compositions containing substances in addition to thiocarbonates, such as a stabilized ammonium tetrathiocarbonate which contains ammonium sulfide, i.e., $(NH_4)_2CS_4 \cdot (NH_4)_2S$. These compositions are generally water soluble and can be prepared, stored, and used in aqueous solutions. The solutions are stable during prolonged periods of storage in a closed container, exhibit low vapor pressure, and are not flammable.

We have also found that the stability of both the concentrated and dilute thiocarbonate solutions can be markedly increased, with respect to $CS_2$ evolution and physical stability, by the addition of a base, sulfide and/or polysulfide. Increases in stability are particularly evident in the more concentrated solutions, i.e. solutions having equivalent $CS_2$ concentrations in excess of 1 weight percent. Aqueous solutions that can be stabilized by the addition of base, sulfide and/or polysulfide include solutions of alkali, alkaline earth and ammonium tri- and tetrathiocarbonates and combinations of these, and very stable alkali metal and alkaline earth metal tetrathiocarbonate solutions can be obtained. Significant stability enhancement can be achieved even in the most concentrated solutions. Thus, significant stability enhancement can be achieved in compositions having equivalent $CS_2$ concentrations of about 1 weight percent or more or even 5 weight percent or a more equivalent $CS_2$ up to the solubility limit of the thiocarbonate in the solution. Typically, the more concentrated solutions (as opposed to the dilute solutions employed in most agricultural practices) have thiocarbonate concentrations corresponding to about 1 to about 20 weight percent equivalent carbon disulfide. The stability and safety of concentrates containing 10 weight percent or more equivalent $CS_2$ can be markedly improved by these procedures.

Stability enhancement can be achieved by providing, in the solution, an organic or inorganic base which, preferably, is soluble in the solution, and more preferably, has significant solubility in water. Presently preferred bases include water-soluble inorganic bases, and the most preferred, are alkali metal and ammonium hydroxides, and combinations of these. Alternatively, similar increases in stability can be achieved by providing, in the solution, a sulfide and/or polysulfide which, preferably, is soluble in the solution, and more preferably, has significant solubility in water. Illustrative sulfides include ammonium, alkali and alkaline earth metal sulfides and polysulfides having the general, empirical formula $M_nS_x$, wherein M is ammonium, alkali or alkaline earth metal, x is at least about 1, preferably greater than 1 in the case of polysulfides, and usually within the range of 1 to about 5, most preferably greater than 1 to about 5, n is 2 when M is ammonium or alkali metal, and n is 1 when M is an alkaline earth metal. Combinations of different sulfides and/or polysulfides can be employed. Thus, combinations of ammonium, alkali and/or alkaline earth metal sulfides and/or polysulfides can be used to stabilize the thiocarbonate compositions, and combinations of the described bases, sulfides and/or polysulfides can be used to achieve further enhanced stability, and are presently preferred. Presently, the most preferred stabilized, thiocarbonate compositions contain added base in addition to one or more of the described sulfides or polysulfides.

Any amount of added base or sulfide, or combination of these, enhances the solution's stability. Thus, the novel compositions comprise aqueous solutions of thiocarbonates containing added base, sulfide and/or polysulfide. Generally, the amount of added base, sulfide or polysulfide will correspond to about 0.01, usually about 0.02, preferably at least about 0.04, and most preferably about 0.08 equivalents of base, sulfide or polysulfide per equivalent of carbon disulfide in the solution. Concentrated, aqueous tetrathiocarbonate solutions having $CS_2$ vapor pressures corresponding to $CS_2$ concentrations in the equilibrium vapor phase below about 1 volume percent at 24° C., i.e. below the explosive limit for carbon disulfide, can be achieved with base concentrations of about 0.02 equivalent of base per equivalent of carbon disulfide. Somewhat higher base concentrations, i.e. at least about 0.08 equivalents of base per equivalent of carbon disulfide, are presently preferred for producing aqueous, trithiocarbonate solutions having $CS_2$ partial pressure corresponding to about 1 volume percent or less carbon disulfide in the equilibrium vapor phase at 24° C. While significant improvements in solution stability and reductions in $CS_2$ partial pressure can be achieved by the use of sulfides and/or polysulfides in the absence of added base, the concentration of sulfide and/or polysulfide required to achieve the desired reduction in $CS_2$ partial pressure (and consequent increase in stability) is generally somewhat higher than the concentration of base required to achieve a similar stability improvement. Thus, in order to obtain a $CS_2$ partial pressure corresponding to a $CS_2$ concentration in the equilibrium vapor phase overlying the solution below 1 volume percent of 24° C., it is presently preferred to employ concentrations of sulfide and/or polysulfide of about 0.04 or more equivalent of sulfide and/or polysulfide per equivalent of carbon disulfide. As in the case of added base, greater solution stability and lower $CS_2$ partial pressures can be achieved by using even higher concentrations of sulfides and/or polysulfides, or by employing combinations of base and sulfide and/or polysulfide. Typically, the concentration of sulfide, polysulfide or combination thereof will correspond to at least about 0.02, preferably at least about 0.04, and most preferably at least about 0.08 equivalent of sulfide and/or polysulfide per equivalent of carbon disulfide. However, when combinations of base and sulfide are employed, the respective concentrations of each can be reduced by approximately $\frac{1}{2}$ to obtain a comparable degree of stability improvement and $CS_2$ partial pressure reduction. In other words, the degree of stability enhancement achieved by the use of 0.02 equivalent of base per equivalent of carbon disulfide, can be achieved by using approximately 0.01 equivalent of base in combination with about 0.01 equivalent of sulfide or polysulfide. The term "equivalent," as employed herein, is used in its conventional sense. Thus, one mole of carbon disulfide constitutes 2 equivalents, and the same is true for the sulfide and polysulfide and for the alkaline earth metal bases and other bases which can be employed in which the cation is divalent. However, one mole of the ammonium and alkali metal bases, wherein the cation is monovalent, constitute only 1 equivalent. Therefore, on a molar basis, as opposed to an equivalent basis, 2 moles of an alkali metal hydroxide, e.g. sodium hydroxide, are equivalent to 1 mole of carbon disulfide.

Accordingly, the amount of base, sulfide and/or polysulfide employed should be sufficient to reduce the carbon disulfide partial pressure of the solution by the desired amount, and the amount of additive required to achieve that effect can be easily determined by adding different, known quantities of base, sulfide and/or polysulfide to the desired thiocarbonate solution, confining the vapor space over the solution at 24° C. for a sufficient period of time, e.g. about 24 hours, and analyzing the vapor phase by gas chromatography for carbon disulfide. Lower additive concentrations will result in somewhat higher $CS_2$ equilibrium concentrations (e.g. higher $CS_2$ partial pressures), and higher additive concentrations will result in lower $CS_2$ partial pressures.

The most preferred compositions, presently, are those in which the carbon disulfide partial pressure has been reduced to a level corresponding to about 1 volume percent or less carbon disulfide in the equilibrium vapor phase at 24° C. A greater safety factor, with regard to $CS_2$ partial pressure, toxicity, handling difficulty, etc., can be realized by reducing $CS_2$ partial pressure even further. Thus, more preferred thiocarbonate solutions are those in which the carbon disulfide partial pressure corresponds to less than about 0.5, most preferably less than about 0.2 volume percent carbon disulfide in the equilibrium vapor phase overlying the solution at 24° C.

Ammonium thiocarbonates can be prepared by the procedures described in Young and Green U.S. Pat. No. 4,476,113, Oct. 9, 1984, the disclosure of which is incorporated herein by reference in its entirety. Briefly, they can be prepared by mixing ammonia, hydrogen sulfide, carbon disulfide, water, and, optionally, sulfur in the proper proportions, and under conditions which facilitate removal of the heat generated during the reaction. Most of this heat results from the mixing of ammonia and hydrogen sulfide, and from the addition of carbon disulfide to the other components. No particular order of component addition is required, except that ammonia must either be present prior to hydrogen sulfide addition or must be added concurrently with the hydrogen sulfide. In a typical batch preparation, the required amount of water will be introduced into a container (which has cooling coils or other heat exchanging means), followed by the sequential additions of gaseous or liquid ammonia and hydrogen sulfide, sulfur (if required), and carbon disulfide.

A stabilized ammonium fumigant which is obtained by the above preparations comprises an aqueous solution of up to about fifty percent by weight solute, in which solute the molarity of hydrogen sulfide is greater than the molarity of carbon disulfide, and is about one-half the molarity of ammonia, and in which sulfur can also be present. Were it not for the requirement that the hydrogen sulfide molarity exceeds that of the carbon disulfide, the range of solute compositions could include the stoichiometric equivalents of ammonium trithiocarbonate and ammonium tetrathiocarbonate. This requirement, in fact, is an important factor in obtaining the enhanced stability exhibited by the compositions of this invention.

Some general parameters which have been determined to effect composition physical stability are as follows for a composition which is an aqueous solution of about 45 percent by weight of a solute comprising hydrogen sulfide, ammonia (at twice the molarity of hydrogen sulfide), carbon disulfide, and sulfur:
  (a) the composition is stable for several months without hydrogen sulfide evolution if (1) sulfur molarity is greater than or equal to carbon disulfide molarity, and (2) hydrogen sulfide molarity is less than 1.5 times the carbon disulfide molarity;
  (b) for the case described above in (a), carbon disulfide will separate into a separate phase if its molarity is greater than that of hydrogen sulfide; and
  (c) the composition is stable for several months without sulfur precipitation if (1) sulfur molarity is less than or equal to carbon disulfide molarity, and (2) hydrogen sulfide molarity is equal to or greater than carbon disulfide molarity.

The solubility limit of an ammonium thiocarbonate composition is approximately 50 to 55 percent by weight solute, showing some variability which is dependent upon relative amounts of the various components present. Release of carbon disulfide is rapidly accelerated upon dilution of the composition with water. Some of the possible compositions of the invention, however, are not suitable for uses which require dilution, because of the resulting sulfur precipitation. In general, sulfur precipitation occurs within a few days if (1) hydrogen sulfide molarity (present with approximately twice its molarity of ammonia) is less than about 1.5 times the molarity of carbon disulfide, and (2) sulfur molarity is greater than carbon disulfide molarity, and (3) carbon disulfide is less than about 2.5 percent by weight in the composition.

As a practical matter, the least tolerable manifestation of physical instability is gas evolution, since this causes stresses on the storage container which could result in releasing toxic and flammable or explosive vapors.

The ammonium thiocarbonate compositions are stabilized by excess sulfur against significant increases in vapor pressure, and against significant solid or immiscible liquid phase formation, during reasonable storage periods, and also maintain acceptable chemical stability during such periods.

Alkaline earth metal (i.e., magnesium, calcium, strontium, and barium) thiocarbonates are somewhat more stable against loss of carbon disulfide than is an ammonium thiocarbonate. Moreover, neither alkaline earth metal nor alkali metal (lithium, sodium, potassium and cesium) thiocarbonate solutions form the phytotoxic thiocyanate species upon decomposition, so such solutions generally are more suitable for long-term storage.

Alkaline earth metal thiocarbonates can be prepared by reacting alkaline earth metal sulfides, either alone or mixed with elemental sulfur (when tetrathiocarbonate is to be prepared), with carbon disulfide, preferably in aqueous media, to directly form aqueous fumigant compositions. Alkaline earth metal sulfides can be generated in situ, by reaction of hydrogen sulfide with an aqueous solution or dispersion of alkaline earth metal salts, oxides, hydroxides, and the like. This same procedure is applicable to preparation of alkali metal thiocarbonates.

The preparation is conveniently carried out at temperatures of about 15° C. to about 35° C., but may be conducted between about 0° C. and the boiling point of carbon disulfide, preferably under an inert or reducing gas atmosphere, to avoid oxidation of sulfur compounds to sulfur oxide moieties such as thiosulfates. Reactants are preferably provided in approximately stoichiometric amounts: one mole of alkaline earth metal sulfide per mole of carbon disulfide, to form alkaline earth metal trithiocarbonate, and one additional mole of elemental sulfur added to form alkaline earth metal tetrathiocarbonate. Products have the empirical formula $M_nCS_x$ wherein n is 1 when M is alkaline earth metal, n is 2 when M is alkali metal, and x is 3, 4 or values between 3 and 4.

The solubility limit for alkali and alkaline earth metal trithiocarbonates in water is approximately 55 percent by weight; the limit for corresponding tetrathiocarbonates is about 45 percent by weight. Solutions are normally diluted with water to concentrations less than about 33 percent by weight to avoid precipitation at low temperatures.

The base-containing compositions of further enhanced stability and reduced $CS_2$ partial pressure can be readily obtained by providing the desired amount of base in the thiocarbonate solution. Base can be introduced into the thiocarbonate solution before, during or after preparation of the thiocarbonate, it being necessary only that the final composition contain additional base. Preferably, such added base is provided either during or after preparation of the thiocarbonate. Similar techniques can be employed to prepare the sulfide- and polysulfide-containing compositions. Thus, the sulfide and/or polysulfide can be introduced into the thiocarbonate solution before, during or after preparation of the thiocarbonate, although such sulfides are preferably added either during or after preparation of the thiocarbonate. Sulfide and polysulfide can be provided in the composition by direct addition of such compounds, or they can be formed in situ. Thus, an amount of base, e.g. sodium hydroxide, can be added followed by addition of an equivalent quantity of hydrogen sulfide to convert the base to the corresponding sulfide, e.g. sodium sulfide ($Na_2S$). The polysulfides can be formed in situ by addition of elemental sulfur with adequate agitation to promote the reaction of the elemental sulfur with the sulfide already present in the composition. Thus, 3 equivalent weights of sulfur can be added to a solution containing 1 equivalent weight of sodium sulfide to produce a composition nominally containing sodium tetrasulfide, i.e. $Na_2S_4$. Similar preparation techniques can be employed with all ammonium, alkali and alkaline earth metal sulfides and polysulfides.

Salts may be recovered from the aqueous solutions by evaporation of the water and filtration of the resulting precipitate (under an inert or reducing atmosphere) if it is desirable to store the thiocarbonate for extremely long periods prior to use as a fumigant. However, the aqueous solution is substantially stable in and of itself; therefore, there is usually no need to recover the salt as a substantially anhydrous solid. Moreover, it is generally easier to handle the liquid solution than the solid thiocarbonate.

The above-described thiocarbonates, and in particular the aqueous, thiocarbonate solutions of enhanced stability and reduced $CS_2$ partial pressure containing added base, sulfide and/or polysulfide, can be used as fumigants or in industrial applications involving the use of thiocarbonate compounds. The stabilized, concentrated compositions are particularly useful for manufacture, storage and transport of concentrated thiocarbonate compositions, particularly when it is desired to avoid the hazards associated with carbon disulfide evolution.

While the above-described thiocarbonates are active fumigants and therefore may be used in any form (e.g., as a powder admixed with inert solids, as solution or dispersion in an organic solvent, etc.), it is preferred to use the aqueous solutions directly as fumigants. Therefore, the fumigation method of the invention may be carried out by the application of aqueous solutions of the thiocarbonates.

The above aqueous reaction solutions may be diluted prior to application as fumigants to provide a solution concentration of as low as 0.01 percent by weight of the thiocarbonate. The aqueous solution may incorporate surfactants to assist in application as a fumigant. Preferably, a strong base, e.g., an alkali metal hydroxide such as sodium hydroxide, is added to the aqueous solution to increase the stability thereof during application.

The alkaline earth metal thiocarbonates (like the ammonium and alkali metal analogues) decompose upon exposure to the atmosphere, at ambient temperatures and humidities, to yield carbon disulfide. Therefore, the aqueous solution will yield (upon evaporation of the water) a solrated alkaline earth metal thiocarbonate which decomposes to carbon disulfide, in the presence of atmospheric gases at ambient temperatures.

The aqueous thiocarbonate solutions utilized in the methods of this invention are stable against significant increases in vapor pressure, and significant solid phase formation, during storage periods. These solutions also maintain acceptable chemical stability during such periods, as measured by their ability to decompose to carbon disulfide upon application as a fumigant.

The stabilized compositions containing added base, sulfide and/or polysulfide have even greater stability, particularly with regard to $CS_2$ evolution, and they are even more preferred in many applications due to that desirable property.

Soil application of a thiocarbonate composition can be accomplished either prior to planting or after plant growth is established. It should be noted, however, that different plant species exhibit differing tolerances to chemical agents. In addition, phytotoxicity to a particular plant can be dependent upon its growth stage. Germination is not inhibited for most plant seeds after soil treatment, and growth of established plants is not significantly altered. Some seedlings, though, show phytotoxicity symptoms. Postplant applications of the composition to such diverse crops as corn, cotton, tomatoes, potatoes and grapes have given no indications of phytotoxicity at effective nematocidal application rates, but cucumber plants have been shown to be somewhat sensitive to thiocarbonate.

The compositions can be applied as fumigants in undiluted form (to minimize the amount which is required per acre) by spraying onto the soil surface, preferably followed within several hours by water application to move the composition into the soil before a significant amount of free carbon disulfide is released. Injection into the soil, using a shank or knife, is also a useful method for applying the compositions. This application can either be "flat," wherein the injectors are closely spaced to treat essentially the entire field area, or can be "localized" by spacing the injectors such that only the plant growing bed is treated, in bands.

Alternatively, those forms of the compositions which are physically stable upon dilution can be mixed into irrigation water and applied by any customary manner, such as through sprinklers, in the water for furrow or flood irrigation, and in drip irrigation systems. The compositions will move into the soil with the water, and decompose to accomplish their fumigation functions, including nitrification inhibition.

Decomposition of the thiocarbonates in the diluted solutions, prior to movement into the soil, can be retarded by increasing the pH of the solutions. With waters having a high total hardness, however, even the inherent alkalinity of thiocarbonate salts can lead to the precipitation of insoluble carbonates, i.e., of calcium, which tend to plug drip irrigation emitters or sprinkler nozzles. Such precipitation can be retarded by the addition of a hardness-complexing agent, such as sodium hexametaphosphate, to the water.

The composition and characteristics of "hard" water have been extensively investigated. As discussed in *The Condensed Chemical Dictionary*, 7th edition, Van Nostrand Rienhold Co., 1966, page 1016, hardwater contains dissolved salts of calcium and magnesium, and the degree of hardness (calcium and magnesium salt content) is often expressed in terms of grains of calcium carbonate per gallon. One grain of calcium carbonate per gallon is equivalent to 17.1 parts per million by weight, and water containing up to about 5 grains of hardness per gallon is considered soft. (All ppm values discussed herein are in parts by weight.) Waters containing over 30 grains (about 500 ppm) are very hard. The "hardness" of irrigation waters can vary considerably, with most irrigation waters containing at least about 50 ppm, generally at least about 100 ppm, and often at least about 200 ppm total hardness (calcium and magnesium carbonate content) expressed as calcium carbonate and can range as high as 1200 ppm or more. The degree of water hardness can be determined by titration with standard base.

Water "hardness" is also often referred to as "temporary hardness," since the compounds (calcium and magnesium compounds, primarily) which result in hardwater deposits are present as bicarbonates, e.g. calcium and magnesium bicarbonate, which convert to insoluble carbonates under some conditions. We have found that addition of the thiocarbonates discussed herein to "hard" irrigation waters results in plugging of constricted irrigation orifices such as drip irrigation emitters and sprinkler nozzles, and that such plugging can significantly impair or completely shut down an entire irrigation system. While complexing agents can reduce or eliminate such plugging problems, such complexing agents must be used in concentrations stoichiometrically equivalent to the concentration of hardwater components, or in higher concentrations.

Surprisingly, we have found that sodium hexametaphosphate (SHMP) significantly reduces and eliminates irrigation system plugging at concentrations well below the stoichiometric equivalent concentration of hardwater components in irrigation water and, also, that it is not hydrolyzed in the thiocarbonate compositions described herein. Sodium hexametaphosphate is known to hydrolyze in the presence of water. However, the absence of such hydrolysis (or markedly reduced hydrolysis rate) in the described thiocarbonate solutions, and the very low concentrations of SHMP required to minimize irrigation system plugging by hardwater deposits make that material particularly effective and attractive for use in combination with the described thiocarbonates when applied by irrigation. For instance, sodium hexametaphosphate concentrations of less than about 10 percent of the equivalent total (stoichiometric) carbonate content in the irrigation solution effectively inhibit irrigation system plugging. Accordingly, SHMP concentrations within the range of about 0.2 to about 10 parts per million in the irrigation solution essentially eliminate plugging problems with all irrigation waters containing the described thiocarbonates. As a result, the provision of sodium hexametaphosphate concentrations of at least about 0.1 weight percent in the described, concentrated thiocarbonate solutions assures that sufficient SHMP will be present when the concentrated thiocarbonate solution is diluted for application by irrigation.

The sodium hexametaphosphate concentration in the diluted irrigation solution should be at least about 0.1 ppm, usually at least about 0.2 ppm, preferably at least about 0.5 ppm, and will generally be within the range of about 0.2 to about 10 ppm. However, as pointed out above, SHMP concentrations can be much less than the equivalent carbonate content of the irrigation solution, which results in significant cost savings and avoids problems which might occur by interaction of substantial amounts of components other than the thiocarbonate, keeping in mind that thiocarbonate stability is of primary importance.

The presence of adequate concentrations of sodium hexametaphosphate in the irrigation solution can be assured by combining that material with the thiocarbonate concentrate prior to dilution. Typically such concentrates should contain at least about 10 ppm, generally at least about 20 ppm, and typically about 20 to more than 1000 ppm SHMP. Sodium hexametaphosphate concentration can also be expressed in terms of equivalent carbon disulfide in the thiocarbonate contained in the solution and, on that basis, sodium hexametaphosphate concentration should correspond to at least about 0.1 percent, preferably at least about 0.5 percent, and typically about 0.1 to about 2 percent of equivalent $CS_2$ in the thiocarbonate.

The thiocarbonates can be combined with other agricultural chemicals to provide a multifunctional product. For example, the stable salts may be combined with solid or liquid fertilizers such as urea, ammonia, ammonium nitrate, calcium nitrate, etc. and other sources of plant nutrients. Since the described thiocarbonates inhibit nitrification, they reduce the rate at which ammoniacal compounds, such as fertilizers, are nitrified in the soil. Ammoniacal fertilizers are well known in the art, and as that term is used herein, it includes ammonia and ammonium-containing compounds as well as ammonia and ammonium compound formers such as urea, biuret, etc. Illustrative ammonium-containing compounds include ammonium nitrate, ammonium sulfate, etc.

The compositions also can be used in non-soil fumigation procedures, such as in the chamber fumigation of commodities which are introduced into commerce. In this type of procedure, dilution of a composition or the application of heat, or both, can be used to promote a rapid decomposition into the fumigant components. Upon termination of the fumigation procedure, vapors in the chamber can be drawn through a scrubbing system, e.g., one containing an alkaline aqueous solution, to remove the fumigant and prevent atmospheric pollution when the chamber is opened.

Another important use of the compositions is as a fumigant for stored grains and other agricultural products. If applied to products which are to be stored, a fumigant composition can be applied simply by spraying into the product as it is being transported to the storage enclosure with a conveyor, auger or other device. The composition can be applied to agricultural products which are already in storage, by spraying onto the exposed products and sealing the storage enclosure.

It is also possible to use the thiocarbonate compositions for fumigating rooms or storage enclosures; this is accomplished by spraying the floor and walls with the composition, and sealing the space until the desired fumigation is accomplished. As an alternative to spraying, a technique similar to chamber fumigation can be used, wherein heat decomposes the composition in an enclosed space.

The fumigating ability of compositions described herein has been expressed primarily in terms of the available carbon disulfide content. It should be noted, however, that other components can contribute to efficacy as a fumigant. Ammonia, for example, is a fungicide for use on harvested grapefruit, lemons, oranges, and on grain for feed use. In addition, sulfur is very widely used as a fungicide- acaricide-insecticide, so any of the compositions of the invention which decompose to form sulfur will have similar properties in addition to the properties attributable to the carbon disulfide content.

Upon dilution, acidification, heating or introduction into the soil (which is a form of dilution), the compositions of the invention break down into their components by a process which can be conceptualized as a physical dissociation. In a soil environment, the inorganic cation, sulfur, and hydrogen sulfide components are rapidly withdrawn into soil particles, and thereby rendered more or less immobile, depending upon soil characteristics, moisture, ambient temperature and the like. Certain of these species will be used as plant nutrients. Carbon disulfide, however, is not tightly bound to the soil and readily migrates to perform the fumigation function.

The invention is further described by the following examples which are illustrative of various aspects of the invention, and are not intended as limiting the scope of the invention as defined by the appended claims.

MODES FOR CARRYING OUT THE INVENTION

Example 1

An ammonium thiocarbonate composition was prepared, using a 12 liter, three-neck, round-bottom flask, fitted with a sealed stirrer, gas delivery tube, and a U-tube manometer. A 5461 gram charge of water was placed in the flask, and 1266 grams of anhydrous ammonia were added with cooling of the flask and stirring. With further cooling, 1266 grams of hydrogen sulfide were added. To the resulting solution were added 595 grams of finely divided sulfur and, with resumed cooling, 1412 grams of carbon disulfide were also added. Stirring was continued while the mixture was maintained at a temperature between about 24° C. and about 38° C. for a period of about one hour. The resulting clear, deep yellow solution had the following composition:

| Component | Weight Percent | Mole Percent |
|---|---|---|
| $NH_3$ | 12.66 | 16.46 |
| $H_2S$ | 12.66 | 8.22 |
| S | 5.95 | 4.11 |
| $CS_2$ | 14.12 | 4.11 |
| $H_2O$ | 54.61 | 67.1 |

This solution had a specific gravity at 21° C. of 1.130, and a crystallization temperature of about −10° C.

Example 2

Solutions corresponding in stoichiometry to an ammoniated ammonium trithiocarbonate were prepared by the procedure of Example 1. Chemical stability was determined at 23° C. by measuring absorbance at wavelengths corresponding to those of the thiocarbonyl group (11.0 microns) and the thiocyanate group (4.85 microns) at the time of preparation and at subsequent times, using Fourier-transform infrared spectrophotometry.

When the infrared data are expressed as the result of thiocarbonyl absorbance divided by the sum of thiocarbonyl absorbance plus thiocyanate absorbance (called "absorbance ratio" in this and subsequent examples), a plot can be made versus elapsed time since composition preparation. The natural logarithm of the absorbance ratio is a linear function of elapsed time, so a linear regression by the method of least squares was used to calculate the equation of this line. By solving the equation for an absorbance ratio of one-half of its original value, the "half-life" of the composition was calculated, and the following results were obtained.

| Composition, mole percent | | | | Absorbance Ratio | Half-Life, |
|---|---|---|---|---|---|
| $NH_3$ | $H_2S$ | $CS_2$ | $H_2O$ | 0, 2, 4.7 Months | Months |
| 9.93 | 4.14 | 4.13 | 81.80 | 1, 0.45, 0.18 | 2.0 |
| 11.57 | 4.13 | 4.13 | 80.16 | 1, 0.42, 0.16 | 1.9 |
| 13.23 | 4.13 | 4.13 | 78.51 | 1, 0.44, 0.19 | 2.2 |

Example 3

Example 2 was repeated with solutions containing sulfur and varying amounts of other components, yielding compositions as tabulated:

| Formula Number | Composition, Mole Percent | | | | |
|---|---|---|---|---|---|
| | $NH_3$ | $H_2S$ | $CS_2$ | S | $H_2O$ |
| 1 | 9.38 | 4.69 | 4.70 | 4.70 | 76.53 |
| 2 | 13.06 | 6.53 | 4.76 | 4.77 | 70.88 |
| 3 | 13.32 | 6.66 | 4.86 | 7.42 | 67.74 |
| 4 | 14.52 | 7.26 | 4.79 | 4.79 | 68.64 |
| 5 | 16.47 | 8.23 | 4.11 | 4.11 | 67.07 |
| 6 | 16.80 | 8.40 | 4.18 | 6.73 | 63.89 |

It should be noted that Formula 1 corresponds stoichiometrically to a solution of ammonium tetrathiocarbonate.

Infrared absorption determinations were made using these compositions giving the following calculated half-lives:

| Formula Number | Absorbance Ratio | | | | Half-life, |
|---|---|---|---|---|---|
| | 0 Months | 5.5 Months | 12 Months | 15 Months | Months |
| 1 | 0.95 | 0.63 | 0.62 | 0.37 | 11.9 |
| 2 | 0.96 | 0.74 | 0.66 | 0.53 | 17.7 |
| 3 | 0.96 | 0.80 | 0.72 | 0.62 | 25.8 |
| 4 | 0.96 | 0.78 | 0.67 | 0.37 | 13.1 |
| 5 | 0.96 | 0.67 | 0.58 | 0.48 | 14.2 |
| 6 | 0.95 | 0.70 | 0.60 | 0.48 | 14.8 |

These data show that increasing the content of soluble sulfide enhances chemical stability, and that a further enhancement can be obtained by increasing the sulfur content.

Example 4

The compositions of Example 3 were evaluated for physical stability by placing the prepared solutions in a closed container and measuring absolute vapor pressure by flashing the liquid into an evacuated chamber connected to an open tube manometer. The following measurements were obtained:

| Formula Number | Absolute Vapor Pressure, mm. Hg | |
|---|---|---|
| | 0 Months | 6 Months |
| 1 | 222 | — |
| 2 | 93 | — |
| 3 | 154 | — |
| 4 | 99 | — |
| 5 | 112 | 274 |
| 6 | 204 | 224 |

All of the formulae had an acceptable vapor pressure at the time of formulation, but the first four formulae became strongly effervescent during storage, rendering the subsequent vapor pressure measurements unreliable. In addition, an unidentified solid formed in the container with Formula 1 prior to the six month measurement.

These data demonstrate the enhancement in physical stability which is attributable to an excess of soluble sulfide in the composition.

Example 5

Using the procedure of Example 2, chemical stability (in terms of solution half-life) was determined over a period of six months for various compositions prepared according to the method of Example 1. In addition, absolute vapor pressure over the liquid in a closed container was measured at the time of preparing the composition, and the following results were obtained.

| Composition, Mole Percent | | | | | Half-life, | Absolute Vapor |
|---|---|---|---|---|---|---|
| $NH_3$ | $H_2S$ | $CS_2$ | S | $H_2O$ | Months | Pressure, mm. Hg |
| 9.74 | 4.87 | 4.64 | 4.64 | 76.11 | 13.0 | 254 |
| 11.66 | 4.87 | 4.64 | 4.64 | 74.20 | 9.1 | 102 |
| 13.60 | 4.86 | 4.63 | 4.63 | 72.28 | 7.6 | 81 |
| 15.52 | 4.86 | 4.62 | 4.62 | 70.38 | 6.6 | 80 |
| 10.70 | 5.34 | 4.65 | 4.65 | 74.65 | 11.9 | 209 |
| 12.81 | 5.34 | 4.65 | 4.65 | 72.56 | 10.9 | 83 |
| 14.94 | 5.34 | 4.65 | 4.65 | 70.44 | 7.6 | 80 |
| 17.05 | 5.34 | 4.65 | 4.65 | 68.35 | 7.2 | 87 |
| 10.77 | 5.38 | 4.68 | 5.62 | 73.54 | 17.2 | 323 |
| 12.91 | 5.38 | 4.68 | 5.62 | 71.41 | 11.8 | 92 |
| 15.04 | 5.38 | 4.68 | 5.62 | 69.31 | 7.8 | 73 |
| 17.19 | 5.38 | 4.68 | 5.62 | 67.17 | 7.0 | 90 |
| 10.85 | 5.43 | 4.72 | 6.61 | 72.34 | 17.7 | — |
| 13.00 | 5.43 | 4.72 | 6.61 | 70.27 | 11.7 | 107 |
| 15.16 | 5.43 | 4.72 | 6.61 | 68.12 | 8.1 | 79 |
| 17.30 | 5.43 | 4.72 | 6.61 | 66.01 | 7.0 | 77 |
| 9.92 | 4.96 | 3.97 | 3.96 | 77.19 | 15.2 | 158 |
| 11.89 | 4.96 | 3.97 | 3.96 | 75.22 | 10.9 | 83 |
| 13.87 | 4.96 | 3.97 | 3.96 | 73.26 | 7.9 | 77 |
| 15.81 | 4.96 | 3.97 | 3.96 | 71.33 | 7.4 | 80 |
| 9.98 | 4.99 | 3.99 | 4.79 | 76.24 | 18.0 | 203 |
| 11.97 | 4.99 | 3.99 | 4.79 | 74.27 | 11.3 | 81 |
| 13.96 | 4.99 | 3.99 | 4.79 | 72.29 | 7.9 | 71 |
| 15.92 | 4.99 | 3.99 | 4.79 | 70.36 | 7.4 | 81 |
| 10.05 | 5.03 | 4.02 | 5.63 | 75.28 | 15.3 | 226 |
| 12.04 | 5.03 | 4.02 | 5.63 | 73.30 | 10.5 | 78 |
| 14.04 | 5.03 | 4.02 | 5.63 | 71.34 | 7.7 | 70 |
| 16.02 | 5.03 | 4.02 | 5.63 | 69.38 | 7.4 | 80 |
| 14.32 | 7.16 | 4.72 | 4.72 | 69.08 | 19.4 | 118 |
| 18.56 | 7.14 | 4.70 | 4.70 | 64.89 | 12.8 | 106 |
| 22.79 | 7.13 | 4.69 | 4.70 | 60.69 | 10.8 | 140 |
| 14.54 | 7.27 | 4.79 | 6.70 | 66.70 | 20.7 | 129 |
| 18.84 | 7.25 | 4.77 | 6.68 | 62.46 | 13.3 | 101 |
| 23.13 | 7.23 | 4.76 | 6.67 | 58.20 | 10.9 | 135 |
| 14.64 | 7.32 | 4.82 | 7.71 | 65.51 | 20.7 | 129 |
| 18.99 | 7.31 | 4.81 | 7.70 | 61.19 | 13.3 | 96 |
| 23.29 | 7.28 | 4.80 | 7.67 | 56.95 | 10.80 | 133 |
| 19.20 | 9.60 | 4.80 | 4.80 | 61.59 | 14.6 | 152 |
| 24.89 | 9.57 | 4.79 | 4.79 | 55.96 | 12.8 | 168 |
| 19.47 | 9.73 | 4.87 | 6.82 | 59.11 | 14.6 | 145 |
| 25.24 | 9.70 | 4.85 | 6.79 | 53.41 | 12.80 | 166 |
| 19.63 | 9.82 | 4.91 | 7.86 | 57.79 | 16.9 | 150 |
| 25.44 | 9.78 | 4.89 | 7.83 | 52.04 | 13.9 | 168 |

Using a multiple linear regression technique, an equation was derived frown the data of this example, which can be used to predict the chemical stability of a composition. The equation (7) is as follows, wherein t is the solution half-life (in months), and X is the mole percentage of its subscripted component:

$$t = -34.5 - 2.7\, X_{NH_3} + 0.053\, X^2_{NH_3} + 16.8\, X_{H_2S} - 0.092\, X^2_{H_2S} - 2.0\, X_{CS_2} + 0.65\, X_S + 0.21\, X_{H_2O} \quad (7)$$

The data fit this equation quite well, as indicated by the regression correlation of 0.95.

A similar regression calculation was performed, using the vapor pressure data, to predict this physical property of a composition. In the following equation (8), ln(VP) is the natural logarithm of the absolute vapor pressure (millimeters mercury), and X is again the mole percentage of the subscripted component.

$$ln(VP) = 1.907 - 0.447\, X_{NH_3} + 0.013\, X^2_{NH_3} + 0.578\, X_{H_2S} - 0.027\, X^2_{H_2S} + 0.258\, X_{CS_2} + 0.0248\, X_S + 0.040\, X_{H_2O} \quad (8)$$

The fit of data was measured by the correlation and a correlation coefficient of 0.86 was obtained.

Example 6

The rate at which carbon disulfide is lost from diluted ammonium thiocarbonate compositions was determined by bubbling nitrogen through the solutions and measuring the carbon disulfide content of the gas which leaves the solution using a mass spectrometer.

In the determination, the solution, corresponding to that of Example 1 (containing 14.1 percent by weight carbon disulfide), was compared to pure carbon disulfide, and to serial dilutions of the Example 1 solution with water, which were 10, 1 and 0.1 volume percent solutions of the original composition. The results are tabulated below, wherein k is the calculated first order rate constant for loss of carbon disulfide, and t is the solution half-life.

| Composition | k (1) hour | t (hours) |
|---|---|---|
| $CS_2$ | 2.0 | — |
| Ex. 1, 100% | 0.003 | 230 |
| Ex. 1, 10% | 0.14 | 5.0 |
| Ex. 1, 1% | 1.09 | 0.6 |
| Ex. 1, 0.1% | 1.35 | 0.5 |

It should be noted that the value of k for the 0.1 percent solution is approximately 70 percent of the value obtained for pure carbon disulfide. Similar results were obtained when various dilutions of other thiocarbonate solutions were tested.

Example 7

The utility of ammonium thiocarbonate compositions as nematocides was demonstrated in a greenhouse experiment with tomato plants. Eighty containers were used, each containing about 500 grams of sterilized sandy loam soil. Each container was given four 5-milliliter injections of extract from nematode-infested pepper roots, one inch below the soil surface, producing an initial population of 2000 root-knot nematode larvae per container.

Twenty treatments were replicated four times, each treatment consisting of solution injection into the soil at a two inch depth. The treatments included each of the six compositions from Example 3 at three levels, plus one level of the known nematocide 1,2-dibromo-3-chloropropane (DBCP), and a control with only water injected. After injection, each container was enclosed in a plastic bag and placed in the shade for three days. Upon removing the bags, the soils were aerated by stirring and were allowed to stand undisturbed for eight additional days. Following an additional aeration, a tomato seedling was planted in each pot.

Each container received 25 milligrams nitrogen (as calcium nitrate) immediately after planting, followed by 2 grams of a slow release complete fertilizer. The plants were harvested after 37 days of growth, and soil was removed from the roots by a gentle washing with water. By use of a magnifying glass, the number of root galls was counted on each plant. Roots and tops were then separated by cutting, oven dried at 80° C. and weighed.

The results are shown in the following table, in which the "Application" represents milligrams of treatment per kilogram of soil, calculated as contained carbon disulfide for the Example 3 solutions. Gall counts and weights are mean values for the four replicates.

| Treatment Solution | Application, ppm | Gall Count | Dry Weight, Grams | |
|---|---|---|---|---|
| | | | Total | Roots |
| None | — | 24.3 | 1.338 | 0.335 |
| DBCP | 50 | 0* | 1.238 | 0.273 |
| 1 | 22 | 1.3* | 0.933 | 0.175 |
| 1 | 43 | 3.8 | 1.058 | 0.178 |
| 1 | 65 | 1.3* | 0.750 | 0.155 |
| 2 | 22 | 8.3 | 1.323 | 0.298 |
| 2 | 43 | 5.3 | 1.393 | 0.325 |
| 2 | 65 | 5.0 | 1.350 | 0.292 |
| 3 | 22 | 6.5 | 1.135 | 0.253 |
| 3 | 43 | 2.0* | 1.505 | 0.325 |
| 3 | 65 | 4.5 | 1.060 | 0.220 |
| 4 | 22 | 4.5 | 1.145 | 0.243 |
| 4 | 43 | 3.3* | 1.458 | 0.303 |
| 4 | 64 | 1.5* | 1.588 | 0.353 |
| 5 | 22 | 7.5 | 1.178 | 0.253 |
| 5 | 43 | 1.0* | 1.930 | 0.415 |
| 5 | 65 | 0.8* | 1.235 | 0.228 |
| 6 | 22 | 6.3 | 1.503 | 0.313 |
| 6 | 43 | 3.5* | 1.688 | 0.368 |
| 6 | 64 | 1.0* | 1.635 | 0.345 |

The gall counts marked by an asterisk are considered to be statistically indistinguishable.

All of the treatments were effective against the nematodes; the degree of control which is provided, as measured by gall counts, apparently is directly dependent upon the application rate, expressed in terms of carbon disulfide content.

No significant phytotoxicity was observed for the stabilized solutions under the conditions shown; strong evidence is seen that Solution 1 (corresponding stoichiometrically to ammonium tetrathiocarbonate) was somewhat phytotoxic at the application rates listed. Further, it should be noted that the stabilized compositions of the invention exhibit a trend toward accelerating tomato plant growth.

Example 8

A calcium tetrathiocarbonate solution was prepared by mixing 115.8 grams of calcium oxide with 585 grams water, and adding, with vigorous stirring, 71.6 grams of hydrogen sulfide, forming a dark green slurry. When 67.4 grams of sulfur had been added, the slurry became dark yellow in color. Addition of 180.7 grams of carbon disulfide produced a deep yellow solution containing 36.5 percent by weight calcium tetrathiocarbonate.

Example 9

Aqueous solutions of alkali metal or alkaline earth metal tri- or tetrathiocarbonates have very high solvency for urea, indicating that eutectic compositions are formed. These combinations are biocidal against bacteria, fungi, nematodes, and insects, while providing a wide range of desirable nitrogen and sulfur fertilizer contents. Furthermore, alkali metal and alkaline earth metal cations, in particular, calcium, magnesium, and potassium, are indispensable plant nutrients. Thus, such compositions may be used to provide the major nutrient requirements of crops, while at the same time protecting the crops against pathogens.

Urea was added to a 41.5 percent, by weight, aqueous solution of calcium tetrathiocarbonate until the solubility limit of urea was reached. At room temperature, the solution dissolved 122 percent by weight urea. The resulting solution was 55 percent urea, 18.6 percent calcium tetrathiocarbonate, and 26.3 percent water, by weight. Thus, the solvency of the aqueous solution of calcium tetrathiocarbonate for urea was at least as great as that of water alone. Similarly, a 46 percent solution of potassium tetrathiocarbonate dissolved 100 percent of its own weight of urea. Similar results were obtained with other tri- and tetrathiocarbonates of alkali metal and alkaline earth metals.

Example 10

It has been found that the stability of dilute aqueous solutions of alkaline earth metal thiocarbonates (as measured by rate of decomposition to yield carbon disulfide) increases with the pH of the solution. Therefore, in irrigation applications, wherein dilute solutions are utilized, it is desirable to provide a base to increase the pH of the irrigation solution. A suitable base may be selected from the group consisting of the alkali metal hydroxides and carbonates, e.g. KOH, NaOH, $K_2CO_3$, $Na_2CO_3$, etc. The base may be added to the water of dilution utilized in making up the irrigation solution or can be incorporated in the aqueous alkaline earth metal thiocarbonate solution. Sufficient base is added to provide an irrigation solution having a pH of at least about 7 and preferably at least about 8. Most preferably, the amount of base added will provide an irrigation solution having a pH of at least about 9.

To demonstrate the effect of pH on evaporative losses of $CS_2$ from thiocarbonates, solutions were injected into a closed bottle containing well stirred citratephosphate buffers, giving a solution concentration of 125 milligrams of thiocarbonate ion per liter. Pure carbon disulfide was also injected, for comparison. A syringe was used to periodically sample air in the bottle, and the air was analyzed by gas chromatography. Half-life times for production of carbon disulfide are summarized in the following table.

| pH | Half-life (minutes) | | |
|---|---|---|---|
| | $CS_2$ | $(NH_4)_2CS_4(NH_4)_2S$ | $CaCS_4$ |
| 5.2 | 1 | 1 | 1 |
| 6.0 | 1 | 1 | 1.8 |
| 7.0 | 1 | 2.1 | 2.7 |
| 8.0 | 1 | 9.2 | 8.0 |
| 9.0 | — | 26.1 | 11.3 |

Results for calcium tetrathiocarbonate at pH values above 7 in this buffer system are unreliable, since calcium phosphates tend to precipitate, causing more rapid dissociation of the thiocarbonate. It is apparent, however, that decomposition for these two compounds proceeds at similar rates.

Example 11

Thiocarbonate solutions were used in a test of their fungicidal properties. Cultures of four plant pathogenic fungi were grown upon potato dextrose agar at room temperature, in diffuse natural lighting. After one week, square blocks having 2 millimeter sides were cut from the edges of actively growing mycelia spots on the agar.

The blocks were immersed in sterile deionized water, as a control, or in dilutions of thiocarbonate solutions using the sterile water, in a closed container. Subsequently, the blocks were removed and placed upon agar in clean plates, and mycelia were allowed to grow for one week.

Radial growth of mycelia colonies was measured for each of the six to eight replicate plates used for a particular fungus, and average colony radius was calculated. Percent control is defined by the following equation:

$$\text{Percent control} = 1 - \frac{\text{Average radius of treated plates}}{\text{Average radius of control plates}} \times 100$$

The results are summarized in the table which follows. Concentrations given for solutions used to treat the agar blocks are expressed in grams of thiocarbonate solution per liter of diluted solution. These results show that the compositions have activity against fungi.

| Treatment | g/l | Percent Control | | | |
|---|---|---|---|---|---|
| | | Fusarium oxysporum | Phytophthora cinnamomi | Verticillium dahliae | Sclerotium rolfsii |
| $K_2CS_4$ | 100 | 76 | 100 | 100 | 100 |
| (9.43% $CS_2$) | 10 | 10 | 68 | 15 | 8 |
| | 1 | 8 | 56 | 27 | 42 |
| $K_2CS_4$ | 100 | 74 | 100 | 100 | 100 |
| +6.1% $NH_3$ | 10 | 83 | 100 | 41 | 59 |
| (8.21% $CS_2$) | 1 | 87 | 100 | 46 | 45 |
| $K_2CS_4$ | 100 | 92 | 100 | 100 | 100 |
| +10.7% urea | 10 | 6 | 97 | 53 | 100 |
| (8.17% $CS_2$) | 1 | 0 | 30 | 77 | 48 |
| $Na_2CS_4$ | 100 | 100 | 100 | 100 | 100 |
| (10.6% $CS_2$) | 10 | 6 | 37 | 26 | 100 |
| | 1 | 4 | 37 | 23 | 54 |
| $Na_2CS_4$ | 100 | 100 | 100 | 100 | 100 |
| +6.1% $NH_3$ | 10 | 14 | —* | 59 | 100 |
| (9.52% $CS_2$) | 1 | 2 | —* | 37 | 48 |
| $Na_2CS_4$ | 100 | 94 | 100 | 100 | 100 |
| +10.7% urea | 10 | 30 | —* | 20 | 100 |
| (9.69% $CS_2$) | 1 | 8 | —* | 8 | 50 |
| $CaCS_4$ | 100 | 100 | 100 | 100 | 100 |
| (2.8% $CS_2$) | 10 | 18 | 56 | 22 | 62 |
| | 1 | 3 | 56 | 13 | 46 |
| $(NH_4)_2CS_4$ | 100 | 100 | 100 | 91 | 100 |
| $(NH_4)_2S$ | 10 | 100 | 74 | 81 | 93 |
| (13.0% $CS_2$) | 1 | 70 | 97 | 41 | 49 |

*contaminated cultures

Example 12

The effect of various application rates of thiocarbonates for pest control was shown in a series of experiments.

Citrus trees were treated with a 32 percent by weight solution of $(NH_4)_2CS_4$ $(NH_4)_2S$ applied evenly to soil around the trunks using a sprinkler can, and thoroughly watered in with flood irrigation. Soil samples taken 30 days following treatment were counted for citrus nematode larvae, giving the results summarized below, where the application rate is expressed in liters per hectare.

| Application | Larvae/500 cc. |
|---|---|
| 0 | 2887 |
| 470 | 325 |
| 940 | 521 |
| 1870 | 1739 |

Example 13

Using a drip irrigation system, grapevines were treated with $(NH_4)_2CS_4$ $(NH_4)_2S$ at a rate of about 43 kilograms per hectare, using three equal treatment applications made at three day intervals. Total control of citrus nematode larvae was obtained over a three-month period.

Example 14

In a laboratory test, it was found that a single application of the composition described in Example 13 produced 96 to 100 percent control of the citrus nematode larvae at an application rate of about 655 kilograms per hectare.

Example 15

Sugar beets, infested with sugar beet cyst nematodes (Heterodera spp.), were treated by application to the soil of about 94 kilograms per hectare of $CaCS_4$, dissolved in irrigation water. Counts of nematode larvae in the soil, following treatment, remained high, but the larvae were not viable, due to parasitism by other soil organisms.

Example 16

In petri dish tests of $CaCS_4$ against the fungus Fusarium spp., control with solutions containing less than about 10 grams per liter of the compound, in both potato dextrose agar and potato dextrose broth, was obtained using the solution when the broth also contained another fungus, Trichoderma spp.

The results of Examples 12 through 16 indicate that control of soil-borne plant parasites can be obtained by applying sub-lethal doses of biocide, that is, amounts which are insufficient to substantially eradicate the pests, but which can weaken the pests and thereby facilitate their control by natural predators in the soil. Decreased long-term control is obtained by higher application rates of biocide, since the higher rates can stimulate an increase in the reproductive effort of an organism; a better initial kill will be followed by, for example, a much larger egg hatch, yielding an actual net increase in parasite population. Very high application rates will effectively eradicate susceptible pests, but may lead to rapid proliferation of less susceptible pests, which may also be undesirable.

Another useful application method initially utilizes only sufficient pesticide to stimulate a large reproductive effort, followed by a high dosage, immediately after the egg hatch, to obtain a maximum pest mortality.

Example 17

Experiments were performed to demonstrate the advantages of applying thiocarbonates to moist soils.

A sandy loam soil was placed in 1-liter glass bottles, fitted with stoppers having fluorocarbon liners and silicone rubber septa, to give a soil depth of about 4 cm. Water was added to the soil, in quantities to obtain 50 and 100 percent soil saturation. Thiocarbonate solution or carbon disulfide was then injected near the bottom of the soil layer, the bottles were promptly sealed, and the air space in the bottles was sampled at intervals with a syringe, for gas chromatographic analysis of $CS_2$. The results are summarized below, wherein degradation time is the number of hours required to achieve the maximum $CS_2$ concentration in the air space.

| Soil Moisture % of Saturation | Compound | Degradation Time, hours |
| --- | --- | --- |
| 0 | $CS_2$ | 3.5 |
| | $(NH_4)_2CS_4$ $(NH_4)_2S$ | 2 |
| | $K_2CS_4$ | 2 |
| | $CaCS_4$ | 4 |
| 50 | $CS_2$ | 3.5 |
| | $(NH_4)_2CS_4$ $(NH_4)_2S$ | 3 |
| | $K_2CS_4$ | 5 |
| | $CaCS_4$ | 5 |
| 100 | $CS_2$ | 3.5 |
| | $(NH_4)_2CS_4$ $(NH_4)_2S$ | 48 |
| | $K_2CS_4$ | 48 |
| | $CaCS_4$ | 48 |

Example 18

The ability of the described thiocarbonate compounds to inhibit nitrification of ammoniacal fertilizers in soil can be illustrated by applying to two separate plots of sandy loam soil a urea solution in irrigation water at a rate corresponding to 200 lbs. urea per acre with sufficient water to increase the soil water content to at least 50 percent. This application can be followed, on one of the plots treated with the urea solution and within one hour of application of the urea solution, with application of an aqueous solution containing 5 weight percent calcium tetrathiocarbonate applied at a rate of 100 liters per acre in sufficient irrigation water to increase the soil water content to 100 percent of saturation. The urea in the soil treated with the calcium tetrathiocarbonate solution will be nitrified more slowly than is the urea in the plot not treated with the thiocarbonate.

Example 19

A series of solutions containing 12.9 weight percent equivalent carbon disulfide as sodium tri- or tetrathiocarbonate were prepared by combining sodium hydroxide, deionized water, sulfur (in the case of tetrathiocarbonate only), hydrogen sulfide and carbon disulfide. In the stoichiometric solutions, the reactants were combined in proportions sufficient to provide sodium tri- or tetrathiocarbonate solutions containing 12.9 weight percent equivalent carbon disulfide without any excess reactant. In addition to the stoichiometric solutions, solutions were prepared with systematically increasing sodium hydroxide concentrations at constant equivalent carbon disulfide concentrations, so that excess base was provided in those solutions in the proportions given in the following table.

The respective solutions were prepared by combining the appropriate amounts of base, water, and elemental sulfur (when used to form the tetrathiocarbonate), in 250 ml. bottles. The contents were then tared, and the appropriate amounts of hydrogen sulfide gas were bubbled in with cooling as necessary to form 100 grams of each of the test solutions. The bottles were then capped with Mininert valves, and the appropriate amount of carbon disulfide was added by injecting with a syringe. All sample bottles were shaken overnight to complete the reaction and were then allowed to equilibrate 3 days at 24° C., and the vapor phase was then sampled and analyzed for carbon disulfide by gas chromotography. The results are reported in the following table and show the effects of increasing base concentrations on carbon disulfide partial pressure (carbon disulfide content of the equilibrium vapor phase). Hydrogen sulfide was not detected in the vapor phase of these formulations at an $H_2S$ detection limit of 100 ppmv.

| REDUCTION OF $CS_2$ PARTIAL PRESSURE WITH BASE ADDITION | | |
| --- | --- | --- |
| | $CS_2$ in Equilibrium Vapor at 24° C., Vol. % | |
| Base[a] | Trithiocarbonate | Tetrathiocarbonate |
| 0.00 | 27.5 | 14.4 |
| 0.02 | 34.2 | 0.87 |
| 0.04 | 30.0 | 0.47 |
| 0.08 | 0.67 | 0.29 |
| 0.12 | 0.16 | 0.27 |

[a]Equivalent of base per equivalent of $CS_2$.

These results demonstrate that excess base significantly reduces the carbon disulfide vapor pressure of both tri- and tetrathiocarbonate solutions, that tetrathiocarbonate solutions have consistently lower $CS_2$ partial pressures than the corresponding trithiocarbonate solutions, and that, in the case of both the tri- and tetrathiocarbonates, the $CS_2$ partial pressure of a concentrated solution containing 12.9 weight percent equivalent carbon disulfide can be reduced to a level significantly below the explosive limit, i.e. nominally corresponding to 1 volume percent $CS_2$ in the equilibrium vapor phase at 24° C.

Example 20

The operation described in Example 19 was repeated with the exception that sodium sulfide ($Na_2S$) was substituted for excess base. The sodium sulfide was introduced by forming solutions containing incrementally greater amounts of sodium hydroxide and then adding additional amounts of hydrogen sulfide equivalent to the amount of excess sodium hydroxide to convert the excess sodium hydroxide to sodium sulfide in situ. The results are reported in the following table:

| REDUCTION OF $CS_2$ PARTIAL PRESSURE WITH SULFIDE ADDITION | | |
| --- | --- | --- |
| | $CS_2$ in Equilibrium Vapor at 24° C., Vol. % | |
| Sulfide[a] | Trithiocarbonate | Tetrathiocarbonate |
| 0.00 | 27.5 | 14.4 |
| 0.02 | 45.9 | 6.60 |
| 0.04 | 1.39 | 0.74 |
| 0.08 | 0.57 | 0.12 |
| 0.12 | 0.42 | 0.13 |

[a]Equivalent of sulfide per equivalent of $CS_2$

These results demonstrate that the carbon disulfide vapor pressure of both tri- and tetrathiocarbonate solutions can be significantly reduced by providing a sulfide in the solution, that the tetrathiocarbonate solutions have consistently lower $CS_2$ vapor pressures than the corresponding trithiocarbonate solutions, and that the $CS_2$ partial pressure of concentrated tri- and tetrathiocarbonates containing 12.9 weight percent equivalent carbon disulfide can be reduced to a level significantly below the explosive limit, i.e. below the level that would form 1 volume percent $CS_2$ in the equilibrium vapor phase at 24° C.

Example 21

The operation described in Example 19 can be repeated using potassium tri- and tetrathiocarbonate solutions containing 12.9 weight percent equivalent carbon disulfide, 0.04 equivalent sodium hydroxide per equivalent II of carbon disulfide, and 0.04 equivalent sodium hydroxide per equivalent carbon disulfide. The thiocarbonate solutions are prepared as described in Example 19 and the amount of sodium hydroxide added in excess of that required to form the thiocarbonate corresponds to 0.08 equivalent sodium hydroxide per equivalent of carbon disulfide (keeping in mind that 1 mole of sodium hydroxide corresponds to 1 equivalent of sodium hydroxide, while 1 mole of carbon disulfide corresponds to 2 equivalents of that component). 0.04 equivalent of hydrogen sulfide is then sparged into the solution, and pressure is maintained on the system with adequate mixing to assure complete reaction of the hydrogen sulfide with a portion of the excess sodium hydroxide to convert 0.04 equivalent of the sodium hydroxide to sodium sulfide ($Na_2S$). The resulting composition will have a significantly lower $CS_2$ partial pressure than an otherwise identical thiocarbonate composition in the absence of the combination of excess base and sulfide under otherwise identical conditions.

Example 22

This example demonstrates the incremental stability improvements realized by the addition of elemental sulfur, and consequent formation of polysulfides, in thiocarbonate compositions.

The half-life of an ammonium tetrathiocarbonate solution containing 32.65 weight percent ammonium tetrathiocarbonate [$(NH_4)_2CS_4$] and 12.62 weight percent equivalent ammonium sulfide was determined to be 14 months at 59° C. as determined by the ability of the aqueous solution to generate carbon disulfide when acidified. Thus, half of the effective carbon disulfide was still retained in the composition after storage for 14 months at 59° C.

The effect of elemental sulfur additions and the addition of free radical scavengers on the half-life of thiocarbonate solutions was determined by an accelerated aging procedure in which the compositions were stored at 84° C. in order to accelerate decomposition and thereby facilitate data acquisition. Incremental additions of 1.0, 3.0 and 5.0 weight percent elemental sulfur were made, and these correspond to 0.16, 0.48 and 0.86 equivalents of sulfur per equivalent of ammonium sulfide, respectively. Since the solutions contained 1 equivalent of ammonium sulfide per equivalent of ammonium tetrathiocarbonate (based on the weight percent values for those components given above), the amount of ammonium polysulfide in the solution corresponded, nominally, to 0.16, 0.48 and 0.86 equivalents polysulfide per equivalent of thiocarbonate for the 3 sulfur concentrations employed. The results are presented in the following table:

| EFFECT OF VARIOUS ADDITIVES ON THIOCARBONATE HALF-LIFE | | |
|---|---|---|
| Additive | Concentration Wt. % | Increase (Decrease) in Half-Life, % |
| Hydroquinone | 0.5 | 0 |
| | 1.0 | (5) |
| | 2.0 | (13) |
| p-Methoxyphenol | 0.5 | 0 |
| | 1.0 | 0 |
| | 2.0 | 0 |
| Citric Acid, Na Salt | 0.5 | 0 |
| | 1.0 | 0 |
| | 2.0 | 0 |
| Ascorbic Acid | 0.5 | 0 |
| | 1.0 | 0 |
| | 2.0 | 0 |
| Elemental Sulfur | 1.0 | 0 |
| | 3.0 | 16 |
| | 5.0 | 22 |
| Triethylamine | 1.0 | 0 |
| | 3.0 | (18) |
| | 5.0 | (22) |
| Urea | 5.0 | 0 |
| | 10.0 | (7) |
| | 20.00 | (13) |

These results demo nitrate that small incremental additions of sulfur produce significant incremental additions in the thiocarbon ate half-life, since only 5 weight percent elemental su 1 fur increased thiocarbonate half-life by 22 percent, whereas the remaining additives, the free radical scavengers, either had no effect or a negative effect on solution stability.

Example 23

Field trials were conducted in a drip irrigation system to determine the effectiveness of minor amounts of sodium hexametaphosphate in preventing drip emitter plugging due to the addition of a thiocarbonate to the irrigation water. Sodium tetrathiocarbonate was used as the illustrative thiocarbonate. Four replicates were performed to provide a basis for statistical analysis and verification of results, and each replicate involved the use of 15 drip emitters operated at an irrigation rate of 2 gallons per hour for about 6 hours. A sodium tetrathiocarbonate solution was injected into the irrigation system of all emitters at a rate sufficient to obtain a sodium tetrathiocarbonate concentration in the irrigation solution of about 1450 ppm, which corresponds to an equivalent carbon disulfide dosage rate of 500 ppm $CS_2$. One set of 4 replicates was performed with the irrigation water alone, 1 set with sodium tetrathiocarbonate in the absence of sodium hexametaphosphate, and 6 sets of 4 replicates each were conducted with various concentrations of sodium hexametaphosphate present in the thiocarbonate injected in the irrigation system or with various concentrations of sodium hexametaphosphate injected into the irrigation system separately from and upstream of the thiocarbonate injection point. The irrigation water composition was as follows:

| | |
|---|---|
| Calcium, mg/L | 69 |
| Magnesium, mg/L | 22 |
| Bicarbonate, mg/L | 310 |
| pH | 7.7 |
| Total dissolved solids, mg/L | 500 |
| Hardness (as CaCO3), mg/L | 263 |
| Alkalinity (as CaCO3), mg/L | 254 |

Each emitter head was weighed before the test was commenced and again after termination of the tests to determine the weight gain attributable to hard water deposit formation, by difference, and the weight gains for the 15 emitters in each trial were combined to obtain the total weight gain for each replicate. Trial conditions and results are given in the following table.

| Treatment | Weight Gain Grams |
|---|---|
| 1. Water Control | 0.12 |
| 2. Na$_2$CS$_4$ w/o SHMP[2] | 0.69 |
| 3. 0.5 ppm SHMP premixed[3] | 0.07 |
| 4. 2.3 ppm SHMP premixed[3] | 0.06 |
| 5. 4.5 ppm SHMP premixed[3] | 0.04 |
| 6. 1 ppm SHMP injected[4] | 0.03 |
| 7. 5 ppm SHMP injected[4] | 0.04 |
| 8. 10 ppm SHMP injected[4] | 0.04 |

[1] SHMP concentrations are after dilution with irrigation water.
[2] SHMP is sodium hexametaphosphate.
[3] SHMP was premixed with thiocarbonate concentrate.
[4] SHMP injected separate from and upstream of thiocarbonate.

The results presented above demonstrate that significant weight gain occurred with the water control alone, and that hard water deposit formation was increased significantly by the presence of the thiocarbonate in the absence of sodium hexametaphosphate. However, every sodium hexametaphosphate treatment, even that of 0.5 ppm, markedly reduced hardwater deposits on the irrigation emitters to a level even below that of the water control alone, i.e. in the absence of the thiocarbonate.

Example 24

The operation described in Example 23 was repeated in a different field using a different water source, the composition and properties of which are given below. All other conditions of the trial were identical to those described in Example 23, with the exception that the trial was continued for about 8 hours.

| | |
|---|---|
| Calcium, mg/L | 85 |
| Magnesium, mg/L | 8.5 |
| Bicarbonate, mg/L | 190 |
| pH | 7.4 |
| Total dissolved solids, mg/L | 500 |
| Hardness (as CaCO3), mg/L | 247 |
| Alkalinity (as CaCO3), mg/L | 156 |

Operating conditions and trial results are given below.

| Treatment | Weight Gain Grams |
|---|---|
| 1. Water Control | 0.06 |
| 2. Na$_2$CS$_4$ w/o SHMP[2] | 0.26 |
| 3. 0.5 ppm SHMP premixed[3] | 0.04 |
| 4. 2.3 ppm SHMP premixed[3] | 0.05 |
| 5. 4.5 ppm SHMP premixed[3] | 0.03 |
| 6. 1 ppm SHMP injected[4] | 0.03 |
| 7. 5 ppm SHMP injected[4] | 0.02 |
| 8. 10 ppm SHMP injected[4] | 0.03 |

[1] SHMP concentrations are after dilution with irrigation water.
[2] SHMP is sodium hexametaphosphate.
[3] SHMP was premixed with thiocarbonate concentrate.
[4] SHMP injected separate from and upstream of thiocarbonate.

Again it can be seen that the presence of the thiocarbonate greatly increased the rate of hardwater formation on the irrigation emitters in the absence of sodium hexametaphosphate and that the presence of sodium hexametaphosphate markedly reduced deposit formation that would otherwise have occurred due to the thiocarbonate.

Example 25

The operation described in Example 24 was repeated, with the only exception that smaller emitters calibrated to transmit 0.5 gallons per hour were employed as test subjects. All other conditions were the same as described in Example 24 using the water source described in Example 24. The operating conditions and results are given below.

| Treatment | Weight Gain Grams |
|---|---|
| 1. Water Control | 0.01 |
| 2. Na$_2$CS$_4$ w/o SHMP[2] | 0.33 |
| 3. 0.5 ppm SHMP premixed[3] | 0.00 |
| 4. 2.3 ppm SHMP premixed[3] | 0.00 |
| 5. 4.5 ppm SHMP premixed[3] | 0.00 |
| 6. 1 ppm SHMP injected[4] | 0.00 |
| 7. 5 ppm SHMP injected[4] | 0.00 |
| 8. 10 ppm SHMP injected[4] | 0.01 |

[1] SHMP concentrations are after dilution with irrigation water.
[2] SHMP is sodium hexametaphosphate.
[3] SHMP was premixed with thiocarbonate concentrate.
[4] SHMP injected separate from and upstream of thiocarbonate.

As in Examples 23 and 24, it can be seen that the addition of the thiocarbonate to irrigation water markedly increased hard water deposit formation and that SHMP addition markedly reduced or even eliminated deposit formation during the course of the trial. The significant reductions in deposit formation in this example (Example 25) are particularly important due to the smaller size of the emitters employed which could be totally plugged if significant amounts of deposits formed on the emitters.

While particular embodiments of the invention have been described, it will be understood, of course, that the invention is not limited thereto, since many obvious modifications can be made, and it is intended to include within this invention any such modifications as will fall within the scope of the appended claims.

Having now described the invention, we claim:

1. An aqueous solution comprising:
   (a) a thiocarbonate selected from the group consisting of ammonium, alkali, and alkaline earth metal tri- and tetrathiocarbonates, and combinations thereof, the thiocarbonate being present in the solution in a concentration less than 55 weight percent;
   (b) an amount of a sulfide sufficient to increase the chemical stability of the thiocarbonate in the solution, the sulfide being selected from the group consisting of alkali and alkaline earth metal sulfides of the formula $M_nS_x$, wherein M is selected from alkali and alkaline earth metals and combinations thereof, x is at least 1, n is 2 when M is alkali metal, and n is 1 when M is an alkaline earth metal, and combinations thereof; and
   (c) an ammoniacal compound.

2. The aqueous solution of claim 1 wherein the ammoniacal compound is selected from the group consisting of urea, biuret, ammonia, ammonium nitrate, calcium nitrate, and ammonium sulfate.

3. An aqueous solution comprising:
   (a) a thiocarbonate selected from the group consisting of ammonium, alkali, and alkaline earth metal tri- and tetrathiocarbonates, and combinations thereof, the thiocarbonate being present in the solution in a concentration less than 55 weight percent;
   (b) an amount of a sulfide sufficient to increase the chemical stability of the thiocarbonate in the solution, the sulfide being selected from the group consisting of alkali and alkaline earth metal sulfides of the formula $M_nS_x$, wherein M is selected from alkali and alkaline earth metals and combinations thereof, x is at least 1, n is 2 when M is alkali metal, and n is 1 when M is an alkaline earth metal, and combinations thereof; and (c) ammonia.

4. The aqueous solution of claim 3 further comprising a hexametaphosphate compound.

5. The aqueous solution of claim 3 further comprising a hexametaphosphate compound in a concentration sufficient to inhibit deposition of hard water deposits.

6. The aqueous solution of claim 3 further comprising a hexametaphosphate compound in a concentration less than the stoichiometric equivalent concentration of the hard water components in the solution.

7. The aqueous solution of claim 3 further comprising a hexametaphosphate compound in a concentration less than about 10 percent of the stoichiometric equivalent concentration of the hard water components in the solution.

8. The aqueous solution of claim 3 further comprising at least about 0.1 ppm of a hexametaphosphate compound.

9. The aqueous solution of claim 3 further comprising sodium hexametaphosphate.

10. The aqueous solution of claim 3 further comprising a water-soluble, inorganic base.

11. The aqueous solution of claim 3 further comprising a water-soluble, inorganic base selected from the group consisting of alkali metal hydroxides and ammonium hydroxide.

12. The aqueous solution of claim 3 comprising less than about 45 weight percent of the thiocarbonate.

13. The aqueous solution of claim 3 comprising less than about 33 weight percent of the thiocarbonate.

14. The aqueous solution of claim 3 having a carbon disulfide concentration in the equilibrium vapor phase of about 1 volume percent or less at 24° C.

15. The aqueous solution of claim 3 having a carbon disulfide concentration in the equilibrium vapor phase of about 0.5 volume percent or less at 24° C.

16. The aqueous solution of claim 3 having a carbon disulfide concentration in the equilibrium vapor phase of about 0.2 volume percent or less at 24° C.

* * * * *